United States Patent
Zhuang et al.

(10) Patent No.: US 7,760,364 B1
(45) Date of Patent: Jul. 20, 2010

(54) SYSTEMS AND METHODS FOR NEAR-FIELD HETERODYNE SPECTROSCOPY

(75) Inventors: Guorong V. Zhuang, Santa Clara, CA (US); John Fielden, Los Altos, CA (US); Christopher F. Bevis, Los Gatos, CA (US)

(73) Assignee: KLA-Tencor Corporation, San Jose, CA (US)

( * ) Notice: Subject to any disclaimer, the term of this patent is extended or adjusted under 35 U.S.C. 154(b) by 83 days.

(21) Appl. No.: 12/256,324

(22) Filed: Oct. 22, 2008

(51) Int. Cl.
*G01B 9/02* (2006.01)

(52) U.S. Cl. .................................. 356/502; 356/237.1
(58) Field of Classification Search ............ 356/237.1, 356/502

See application file for complete search history.

(56) References Cited

U.S. PATENT DOCUMENTS

| | | | |
|---|---|---|---|
| 6,888,632 B2 | 5/2005 | Smith | |
| 7,239,390 B2 | 7/2007 | Smith | |
| 2007/0188762 A1 | 8/2007 | Smith | |
| 2009/0272191 A1* | 11/2009 | Maris et al. | 73/618 |

FOREIGN PATENT DOCUMENTS

| WO | WO 2004/048943 A1 | 6/2004 |
|---|---|---|
| WO | WO 2004/048944 A1 | 6/2004 |
| WO | WO 2004/048945 A1 | 6/2004 |
| WO | WO 2006/111942 A1 | 10/2006 |
| WO | WO 2007/049259 A1 | 5/2007 |
| WO | WO 2007/049260 A1 | 5/2007 |

OTHER PUBLICATIONS

Barsegova et al. "Controlled fabrication of silver or gold nanoparticle near-field optical atomic force probes: Enhancement of second-harmonic generation," Applied Physics Letters, vol. 81, No. 18, Oct. 28, 2002, pp. 3461-3463.

Crozier et al. "Optical antennas: Resonators for local field enhancement," Journal of Applied Physics, vol. 94, No. 7, Oct. 1, 2003, pp. 4632-4642.

Fromm et al. "Exploring the chemical enhancement for surface-enhanced Raman scattering with Au bowtie nanoantennas," The Journal of Chemical Physics, vol. 124, 2006, 4 pgs.

(Continued)

*Primary Examiner*—Hwa S. A Lee
(74) *Attorney, Agent, or Firm*—Bever, Hoffman & Harms, LLP; Jeanette S. Harms

(57) ABSTRACT

In a near-field heterodyne spectroscopy system, a near-field generation device receives the output of a pump beam source and is also made to vibrate or move at a frequency f to generate a modulated near-field beam having a near-field component. The outputs of the pump beam source and a probe beam source (optional) as well as the modulated near-field beam are directed to the same point on a sample. At least one of the outputs of the pump beam source and probe beam source is modulated at a frequency $\Omega$. Thus, the reflected beam that results from the interaction with the region illuminated by the modulated near-field beam is modulated at frequencies $\Omega+f$ and $\Omega-f$. Because the excitation is near-field, the electric field in the sample is evanescent and ensures a shallow probing depth as well as smaller lateral dimensions beyond diffraction limit.

36 Claims, 5 Drawing Sheets

OTHER PUBLICATIONS

Fu et al. "Plasmonic microzone plate: Superfocusing at visible regime," Applied Physics Letters, vol. 91, 2007, 3 pgs.

Grbic et al. "Near-Field Focusing Plates and Their Design," Submitted to IEEE Transactions on Antennas and Propagation, Feb. 1, 2008, 11 pgs.

Guo et al. "Plasmonic very-small-aperture lasers," Applied Physics Letters, vol. 91, 2007, 3 pgs.

Haefliger et al. "Contrast and scattering efficiency of scattering-type near-field optical probes," Applied Physics Letters, vol. 85, No. 19, Nov. 8, 2004, pp. 4466-4468.

Hartschuh et al. "Near-field Raman spectroscopy using a sharp metal tip," Journal of Microscopy, vol. 210, Jun. 2003, pp. 234-240.

Hillenbrand et al. "Material-specific mapping of metal/semiconductor/dielectric nanosystems at 10 nm resolution by backscattering near-field optical microscopy," Applied Physics Letters, vol. 80, No. 1, Jan. 7, 2002, pp. 25-27.

Ishihara et al. "Terahertz-wave near-field imaging with subwavelength resolution using surface-wave-assisted bow-tie aperture," Applied Physics Letters, vol. 89, 2006, 3 pgs.

Knoll et al. "Near-field probing of vibrational absorption for chemical microscopy," *Nature*, vol. 399, May 13, 1999, pp. 134-137.

Lerman et al. "Applying solid immersion near-field optics to Raman analysis of strained silicon thin films," Applied Physics Letters, vol. 89, 2006, 3 pgs.

Lieberman et al. "A fully integrated near-field optical, far-field optical, and normal-force scanned probe microscope," Rev. Sci. Instrum. 67 (10), Oct. 1996, pp. 3567-3572.

Merlin, R. "Radiationless Electromagnetic Interference: Evanescent-Field Lenses and Perfect Focusing," *Science*, vol. 317, Aug. 17, 2007, pp. 927-929.

Sundaramurthy et al. "Field enhancement and gap-dependent resonance in a system of two opposing tip-to-tip Au nanotriangles," Physical Review B 72 (2005) 6 pgs.

Sundaramurthy et al. "Toward Nanometer-Scale Optical Photolithography: Utilizing the Near-Field of Bowtie Optical Nanoantennas," Nano Letters 2006, vol. 6, No. 3, pp. 355-360.

Zengerle et al. "All-angle beam refocusing in nonuniform triangular photonic crystal slabs," Journal of the Optical Society of America, vol. 24, No. 4, Apr. 2007, pp. 997-1003.

* cited by examiner

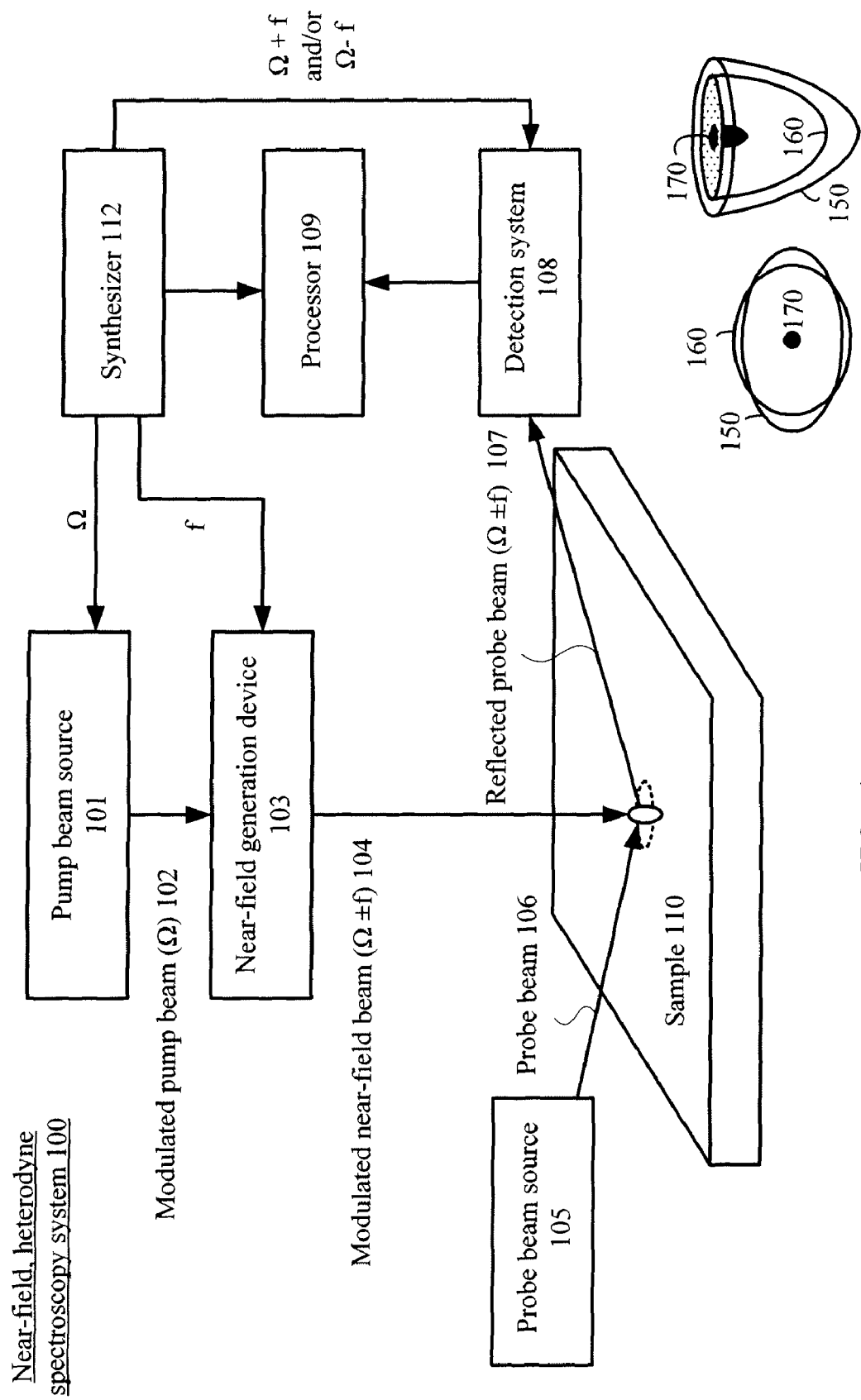
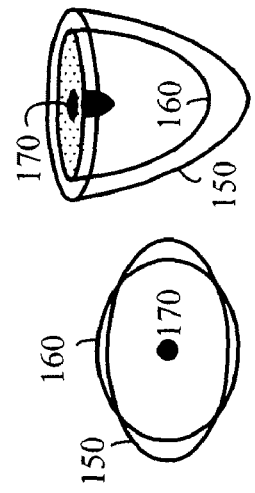
FIG. 1A
FIG. 1B  FIG. 1C

SYSTEMS AND METHODS FOR NEAR-FIELD HETERODYNE SPECTROSCOPY

BACKGROUND OF THE INVENTION

1. Field of the Invention

The present invention relates to spectroscopy and in particular to a near-field heterodyne spectroscopy that facilitates small spot measurement while minimizing probing depth and eliminating background signal in the detection field.

2. Description of the Related Art

Semiconductor metrology, such as monitoring thin film thickness, microstructures, carrier concentration, and strain/stress, is based on electromagnetic wave interaction and its electric field effects on the dielectric function of the material. As the size of the semiconductor device feature shrinks to submicron scale, contactless, non-invasive metrology tools that rely on electromagnetic wave spectrum (spanning from deep ultraviolet (DUV) to far-infrared (THz wave)) to determine material properties face challenges in meeting the spatial resolution imposed by the feature size while still offering sufficient sensitivity.

Photo-reflectance modulation spectroscopy uses the dielectric response of a material from electromagnetic waves to measure specific properties of the material. The spectral response of the material can be modulated by applying an external repetitive perturbation of electromagnetic waves (i.e. a pump beam). The response to the electromagnetic waves can be detected by a reflected probe beam. Specifically, differential changes in the reflectivity can be related to the perturbation of the complex dielectric function $\in = \in_1 + i\in_2$ (wherein $\in_1$ is the real part of permittivity and $\in_2$ is the imaginary part of permittivity) via the following relation:

$$\frac{\Delta R(\lambda)}{R(\lambda)} = \alpha \Delta \varepsilon_1(\lambda) + \beta \Delta \varepsilon_2(\lambda), \quad \frac{\Delta R}{R} = 10^{-4} \sim 10^{-6}$$

and is capable of detecting wherein $R(\lambda)$ is the spectral reflectivity, $\Delta R(\lambda)$ is the spectral change of that reflectivity resulting from frequency modulation, and $\alpha$ and $\beta$ are the Seraphin coefficients. The modulation frequency and wavelength of the pump beam could be optimized for specific applications, e.g. determining material properties, thickness, strain in the thin film, and dopant concentration. However, of severe limitation of the current photo-reflectance modulation techniques is the spatial resolution, i.e. both the lateral and longitudinal dimensions of the sample to be probed by the electromagnetic waves.

Known spectroscopy techniques use a far-field mode, i.e. the distance (L) between sample and pump/probe beam is much larger than the wavelength ($\lambda$), i.e. L>>$\lambda$. In these techniques, both the pump beam and the probe beam are focused by conventional diffraction limited optical elements, e.g. lens, beam splitters, and mirrors.

Unfortunately, in a far-field mode, the spatial resolution is diffraction limited (in practice for metrology, the diffraction limit is much bigger than that given by the Rayleigh criterion because the tails of the response function significantly affect quantitative measurement results):

$$d = \frac{1.22\lambda}{NA}$$

where d is the lateral spatial resolution, $\lambda$ is the wavelength, and NA (the numerical aperture) is equal to n sin $\theta$, where $\theta$ is half of the angular aperture on the object side and n is the refractive index of the medium above the target. Additionally, when using a far-field mode, the penetration depth of the electromagnetic wave in the material is limited by the wavelength either of pump beam or probe beam used (whichever is the shortest). For a laser-based, photo-reflectance system, the penetration depth $\delta$ of light into a non-absorbing material is related to wavelength $\lambda$ as follows:

$$\delta_p = 2.53 \frac{\lambda}{(NA)^2}$$

For an absorbing material, the penetration depth is related to the wavelength ($\lambda$) and extinction coefficient k($\lambda$) of material as follows:

$$\delta_p = \frac{\lambda}{2\pi k}$$

Thus, the minimum measurement site size is limited by the diffraction and penetration of the probe and pump beams.

Notably, because both the probe beam and pump beam are far-field in nature, the scattered luminescence signal from the non-monochromatic pump beam and any background luminescence will be inadvertently collected by the probe beam optics, thereby degrading the signal-to-noise (S/N) ratio.

SUMMARY OF THE INVENTION

A near-field heterodyne spectroscopy system can advantageously provide very small spot measurement (i.e. smaller than the dimension imposed by the diffraction limit) from the wavelength used (e.g. spanning from DUV to THz in electromagnetic spectrum). In one embodiment, the near-field, heterodyne spectroscopy system can include a probe beam source, a pump beam source, a near-field generation device, a detection system, and a processor. The probe beam source can direct a probe beam to a point on a sample where a measurement is desired. The pump beam source can receive a frequency modulation (e.g. from a synthesizer) and deliver a modulated pump beam. The intensity and/or polarization state as well as the phase of the pump beam may be modulated at frequency $\Omega$. The modulated pump beam is then directed to the same point on the sample as the probe beam.

In this embodiment, the near-field generation device receives the modulated pump beam and is also made to vibrate or move at a frequency f to generate a modulated near-field beam having a near-field component. The resulting modulated near-field beam is directed to the same point on the sample as the probe and pump beams, albeit to a nano-scale region within that point. A reflected probe beam that results from the interaction with the region illuminated by the modulated near-field beam is modulated at frequencies $\Omega + f$ and $\Omega - f$ (or, equivalently, f−$\Omega$ if f>$\Omega$), whereas the portion of the reflected probe beam that results from the interaction with the larger region illuminated directly by the modulated pump beam is modulated at frequency $\Omega$.

The detection system can receive the reflected probe beam from the point on the sample, wherein the reflected probe beam results from the probe beam interacting with the region of the sample illuminated by the pump beam and the smaller region illuminated by the near-field beam. At this point, a processor can perform demodulation of the detected reflected probe beam and analyze the sample based on the demodulation.

In another embodiment of a near-field heterodyne spectroscopy system, the pump beam source directs a pump beam at a point on a sample, whereas the probe beam source directs a modulated probe beam having a frequency modulation $\Omega$ at the same point. The near-field generation device, which receives the pump beam, is made to vibrate or move at a frequency f to generate a modulated near-field beam having a near-field component. The resulting modulated near-field beam is directed to the same point on the sample as the pump and modulated probe beams, albeit to a nano-scale region within that point. Therefore, the detection system detects the reflected probe beam that results from the interaction of the modulated probe beam with the region of the sample illuminated by the modulated near-field beam.

In yet another embodiment, a near-field, heterodyne spectroscopy system operates without a probe beam source. In this embodiment, the pump beam source can deliver a modulated pump beam modulated at frequency $\Omega$. The near-field generation device, which receives the modulated pump beam, can be vibrated or moved at a frequency f and deliver a modulated near-field beam having a near-field component modulated at frequencies $\Omega+f$ and $\Omega-f$. The detection system can receive a reflected pump beam from the illuminated region on the sample, wherein the reflected pump beam results from the pump beam interacting with the region of the sample illuminated by the pump beam and the near-field beam. The component of the reflected pump beam resulting from the interaction of the near-field beam with the sample will be modulated at frequencies $\Omega+f$ and $\Omega-f$. The detection system will detect one, or both, of these frequency components of the reflected beam.

In one embodiment, the near-field generation device can include a field enhancement tip device, e.g. a laser-irradiated nanometer-scale tip, or a laser-irradiated nanometer-scale particle attached to the end of AFM tip. In another embodiment, the near-field generation device can include a nanometer-scale "bowtie" antenna. In yet another embodiment, the near-field generation device can include a laser diode device, e.g. an aperture surrounded by rings that resonantly excite surface plasmon polarions. In yet another embodiment, the near-field generation device can include a plasmonic micro zoneplate. In yet another embodiment, the near-field generation device can include a two-dimensional photonic-crystal-based superlens.

To optimize the pump beam, any of the above-described near-field, heterodyne spectroscopy system can further include a beam conditioning optical system that conditions the pump beam for the near-field generation device. In one embodiment, the beam conditioning optical system can include a photonic crystal negative refractive index lens that generates a dark-field image. In another embodiment, the beam conditioning optical system can include a ring aperture.

In one embodiment, the beam conditioning optical system can include an area beam reflector, optics, and a photonic crystal negative refractive index lens. The photonic crystal negative refractive index lens can focus a beam (e.g. a modulated pump beam) onto a sample and generate a dark-field image. The optics can collect the dark field optical signal and direct them to detection system. The area beam reflector can receive and direct the beam to the optics. In one embodiment, the beam conditioning optical system can further include an interferometer that uses an optical feedback through the optics to ensure that the beam conditioning system maintains a predetermined distance from the sample.

Any of the embodiments described herein may be used for measuring films and structures on substrates. The measurements may include, but are not limited to, measuring properties such as thickness, film composition, strain, carrier mobility, carrier density, critical dimensions and overlay. Specifically, the disclosed embodiments could be used to measure local stress in shallow-trench-isolation (STI) and Silicon-On-Insulator(SOI) structures. Near-field Raman spectroscopy as disclosed herein may also be used for measuring strain, stress, composition and local order in advanced nano-structured materials, such as carbon nanotubes and graphene sheets, group III-V compounds like gallium arsenide, group II-VI compounds, organic materials, or mixtures of such materials.

The above-described near-field, heterodyne spectroscopy systems advantageously provide excitation that is near-field by nature, which results in an electric field in the sample that is evanescent. Therefore, the probing depth is shallower than that of far-field excitation. With luminous material or high-scatter material, the near-field excitation techniques can also advantageously eliminate background signals getting into the detector.

BRIEF DESCRIPTION OF THE DRAWINGS

FIG. 1A illustrates an exemplary near-field, heterodyne spectroscopy system.

FIGS. 1B and 1C illustrate the "point" of the sample illuminated by outputs of the pump beam source and the probe beam source (when used) and the smaller region illuminated by the output of the near-field beam generation device.

DETAILED DESCRIPTION OF THE DRAWINGS

Figure 1D:
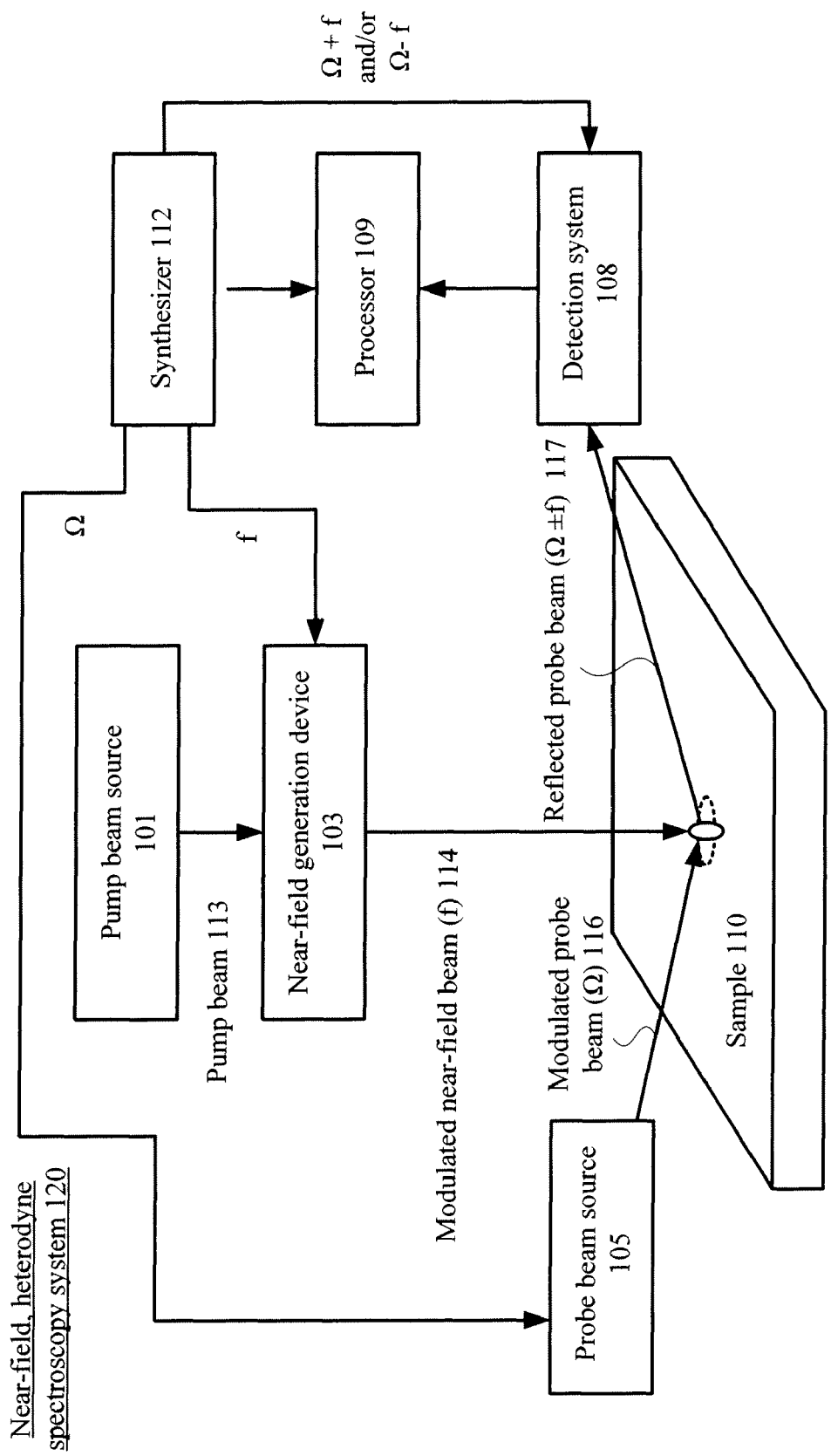
FIG. 1D illustrates another exemplary near-field, heterodyne spectroscopy system.

The dielectric function relates to the electrical properties of a material, e.g. its band structure including density of states, band gap, mobility, and free carrier concentration. The optical properties of a material (including refractive index) also depend on the material's dielectric function. The electrical and optical properties of the materials can be modified during semiconductor manufacturing process (both deliberately and as side effects of other processes) by, among other factors, doping and strain. The in-line metrology of such electrical properties will be increasingly important in future generation semiconductors to optimize their performance. Unfortunately, as device geometries shrink, large-scale test structures (e.g. on the order of μm) may fail to accurately predict the behavior at the transistor level. As described herein, near-field, heterodyne spectroscopy can advantageously overcome the limitations of existing far-field and near-field measurement techniques and thereby facilitate cutting edge semiconductor metrology.

In accordance with one aspect of an improved heterodyne spectroscopy system, a near-field generation device can be included. Note that as used herein, the term "near-field" is defined as a volume with dimensions less than $10\lambda$, where $\lambda$ is the wavelength of the electromagnetic radiation used. FIG. 1A is a block diagram illustrating an exemplary near-field, heterodyne spectroscopy system 100. In system 100, a pump beam source 101 receives a frequency $\Omega$ from a synthesizer 112 and generates a modulated pump beam 102 that is modulated at frequency $\Omega$. Pump beam source 101 could comprise a monochromatic light source such as a laser, or could comprise a broad-band source such as an arc-lamp, a plasma light source, a supercontinuum light source, a quartz-halogen lamp or a glow-bar black-body radiation source. Pump beam source 101 may contain focusing optics, or focusing optics (not shown) may be placed between pump beam source 101 and a near-field generation device 103. Near-field generation device 103 receives modulated pump beam 102 as well as a frequency f from synthesizer 112, which causes near-field generation device 103 to vibrate, move, or otherwise apply an additional modulation to the near-field beam at a frequency f.

As a result of the interaction between modulated pump beam 102 modulated at frequency $\Omega$ and near-field generation device 103 modulated at frequency f, a modulated near-field beam 104 (generated by near-field generation device 103) will contain components at frequencies $\Omega \pm f$, wherein $\Omega$ can be characterized as a carrier frequency and the sidebands of such carrier frequency are of interest, as explained below (or, equivalently, if $f > \Omega$, modulated near-field beam 104 will contain components at frequencies $f \pm \Omega$, wherein f can be characterized as a carrier frequency). Synthesizer 112 controls the amplitude, frequency, and/or phase of the signals used to modulate pump beam source 101 and near-field generation device 103. Modulated near-field beam 104 impinges on a sample 110.

In FIG. 1A, the vertically-oriented ellipse on sample 110 denotes the electric field distribution generated by near-field generation device 103 using modulated pump beam 102, whereas the horizontally-oriented dotted ellipse denotes the region of sample 110 directly illuminated by modulated pump beam 102. Note that the spread of modulated pump beam 102 is typically about 10× or more larger than the spread of modified near-field beam 104.

Concurrently, a probe beam source 105 generates a probe beam 106 (any form of radiation, visible, ultraviolet, infrared, monochromatic, polychromatic, etc.) that impinges on sample 110 at the same point as near-field generation beam 104 (albeit with a much larger spread). FIGS. 1B and 1C illustrate top and perspective views, respectively, of such a "point". In this point, area 150 denotes an exemplary spread of probe beam 106, area 160 denotes an exemplary spread of modulated pump beam 102, and area 170 denotes the spread of near-field beam 104. Notably, area 150 includes information regarding probe beam 106, whereas area 160 advantageously includes information regarding frequency $\Omega$ and frequency f, and of particular interest, $\Omega + f$ and $\Omega - f$. In one, non-limiting embodiment, frequency $\Omega$ is a higher frequency than frequency f, wherein frequency $\Omega$ can be characterized as a carrier frequency and the sidebands of such carrier frequency, i.e. $\Omega \pm f$, are of interest, as explained below.

Note that depending on what material property is being analyzed, a certain type of radiation can be selected for either probe beam 106 or modulated pump beam 102, which is well-known to those skilled in the art of spectroscopy. Exemplary references teaching this selection include, for example, Pub. No. WO/2004/048943, entitled "An Optical Spectrometer", filed on Nov. 27, 2003; Pub. No. WO/2004/048944, entitled "An Optical Measurement Apparatus And Method", filed on Nov. 27, 2003; Pub. No. WO/2004/048945, entitled "Apparatus For Modulating A Light Beam", filed on Nov. 27, 2003; WO/2006/111942, entitled "An Optical Inspection Apparatus And Method", filed on Apr. 10, 2006; WO/2007/049259, entitled "An Optical Measurement Apparatus And Method", filed on Oct. 24, 2006; WO/2007/049260, entitled "An Optical Measurement Apparatus And Method", filed on Oct. 24, 2006; U.S. Pat. No. 6,888,632, entitled "Modulated Scatterometry", issued on May 3, 2005, U.S. Pat. No. 7,239,390, entitled "Modulated Scatterometry", issued on Jul. 3, 2007; and US Publication 2007/0188762, entitled "Modulated Scatterometry", filed on Jan. 24, 2007.

Probe beam source 105 may comprise optics to focus probe beam 106 to an area on sample 110 substantially overlapping with the area where modulated near-field beam 104 impinges on sample 110, or focusing optics (not shown) may be placed between probe beam source 105 and sample 110 to perform the same function. In some embodiments, common focusing optics may be employed to focus both probe beam 106 and pump beam 102. In other embodiments, separate optics may be employed to focus these beams separately.

A reflected probe beam 107, which results from overlapping modulated pump beam 102, modulated near-field beam 104, and probe beam 106 impinging on sample 110, is detected by a detection system 108. A processor 109, which receives inputs from synthesizer 112 and detection system 108, can perform the demodulation of reflected probe beam 107 and then proceed to the analysis of sample 110 based on such demodulation. The exemplary near-field, heterodyne spectroscopy system 100 shown in FIG. 1A is one embodiment for photoreflectance spectroscopy.

FIG. 1D illustrates another near-field heterodyne spectroscopy system 120 in which a pump beam 113 is not modulated. Near-field generation device 103 receives pump beam 113 as well as a frequency f from synthesizer 112 that causes near-field generation device 103 to vibrate, move, or otherwise apply a modulation to its generated near-field beam 114 at a frequency f.

Probe beam source 105 receives a modulation frequency $\Omega$ from synthesizer 112 and generates a modulated probe beam 116 modulated at frequency $\Omega$ that is incident on sample 110 in an area that substantially includes the area where modulated near-field beam 114 is incident. Probe beam 116 may use any form of radiation, e.g. visible, ultraviolet, infrared, monochromatic, polychromatic, etc. Note that depending on what material property is being analyzed, a certain type of radiation can be selected for either modulated probe beam 116 or modulated near-field beam 114, which is well-known to those skilled in the art of spectroscopy.

A reflected probe beam 117, which results from overlapping modulated near-field beam 114 and modulated probe beam 116 impinging on sample 110, is detected by detection system 108. The volume of the sample where probe beam 116 and near-field beam 114 overlap will give rise to a reflected probe beam 117 containing components oscillating at frequencies $\Omega \pm f$ (assuming $\Omega > f$) or frequencies $f \pm \Omega$ (if $f < \Omega$). Processor 109, which receives inputs from synthesizer 112 and detection system 108, can perform the demodulation of reflected probe beam 117 and then proceed to the analysis of sample 110 based on such demodulation. Near-field, heterodyne spectroscopy system 120 is another embodiment for photoreflectence spectroscopy.

Figure 1E:
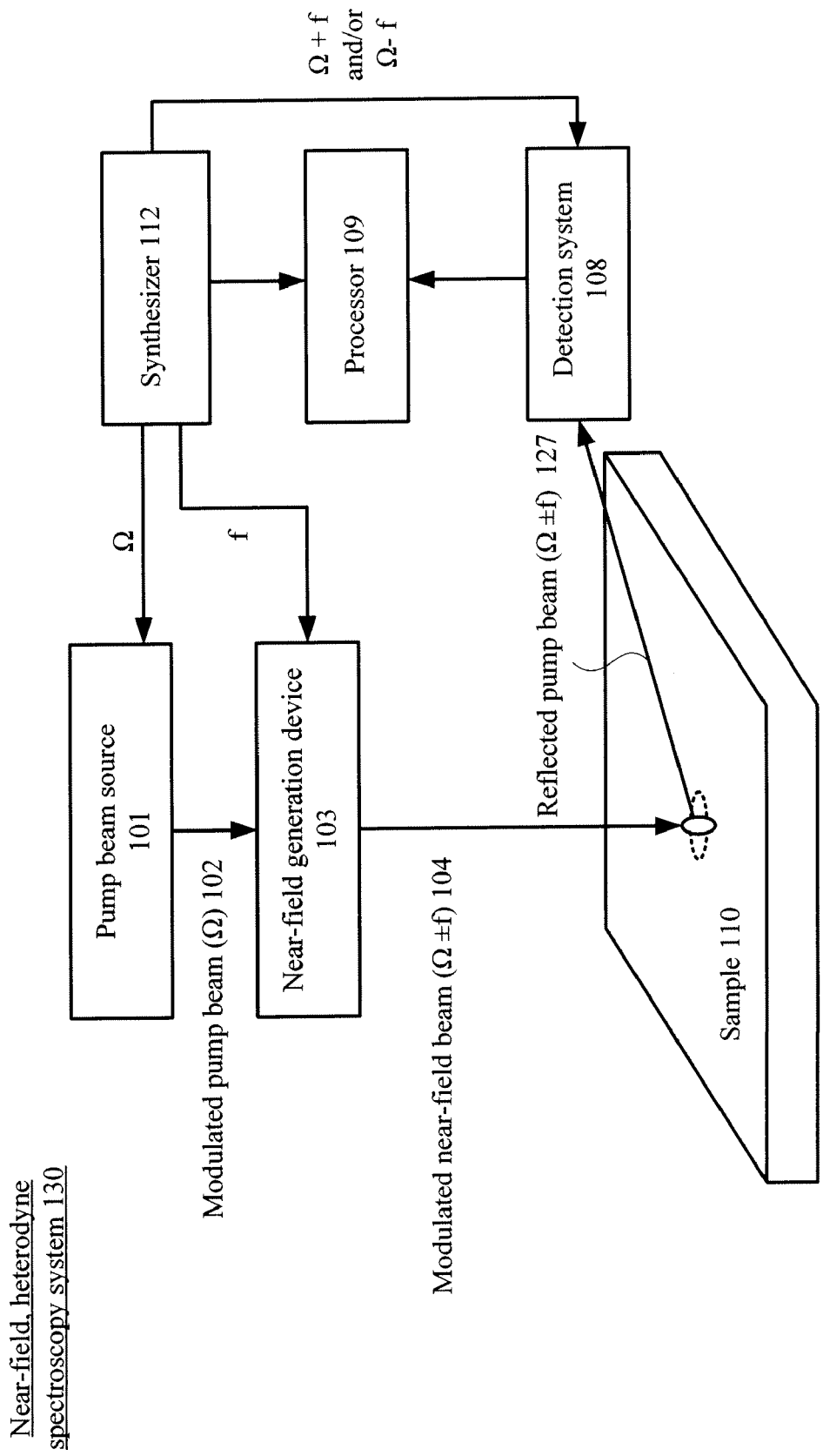
FIG. 1E illustrates another exemplary near-field, heterodyne spectroscopy system.

FIG. 1E shows another near-field, heterodyne spectroscopy system 130. Note that system 130 is similar to that of system 100, but does not include a probe beam source. However, a reflected pump beam 127 still contains components at frequency Ω as well as at additional frequencies Ω+f and Ω−f, wherein Ω can be characterized as the carrier frequency.

Note that demodulation of the reflected beams from sample 110 (e.g. reflected probe beam 107, reflected probe beam 117, or reflected pump beam 127) includes distinguishing between the information provided by areas 170 and 160 (FIGS. 1B and 1C). For example, the demodulation techniques disclosed in U.S. Pat. Nos. 7,239,390 and 6,888,632, which are incorporated by reference herein, can be used in processor 109 for systems 100, 120, or 130. Specifically, the detected signal can be characterized as a modulated near-field portion of a signal (area 170) superimposed on a far-field background (area 160). Demodulation by processor 109 in system 130 can further include enhancing the near-field signal relative to far-field signal, thereby facilitating the determination of the sum frequency (f+Ω) and/or the difference frequency (Ω−f).

Note that although the near-field generation device is shown in the path of the pump beam or the modulated pump beam (designated a generic pump beam herein) the generic pump beam still impinges on sample 110. The generic pump beam and the generic probe beam (i.e. the probe beam or the modulated probe beam, as provided in the embodiment) have similar dimensions (e.g. between 1 micron and 1 mm) and substantially overlap. Notably, both the generic pump beam and the generic probe beam are aimed at substantially the same point on sample 110, which is the point that the modulated near-field beam impinges on sample 110.

Depending on the wavelengths of the generic pump and probe beams, one or both generic beams may interact with near-field generation device 103. For example, if near-field generation device 103 is a gold sphere of nm dimensions mounted on the end of an AFM tip, then that sphere will strongly enhance visible wavelengths, but ultra-violet (UV) wavelengths will experience little, or no, enhancement. In this example, if the generic pump beam is at a visible wavelength such as 532 nm and the generic probe beam is a near UV beam using wavelengths in the range of about 330-450 nm, then only the generic pump beam will generate a strong near field around the tip. If both generic beams are at visible wavelengths, then both generic beams would generate strong near fields around the tip, which would typically result in a stronger signal from the volume of interest. One generic beam would be modulated at frequency f, whereas the other generic beam would contain components at Ω±f. In this manner, the reflected beam, in addition to components at Ω and) Ω±f may also contain components modulated at Ω±2f, which may in some applications provide additional information or discriminatory ability.

Figure 2C:
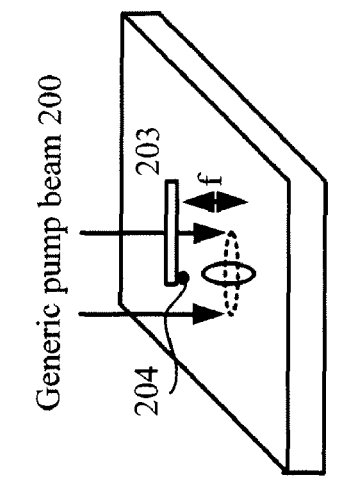
FIG. 2C illustrates an exemplary near-field generation device as implemented by attaching a nano-particle to a tip as enhancement device.
Figure 2B:
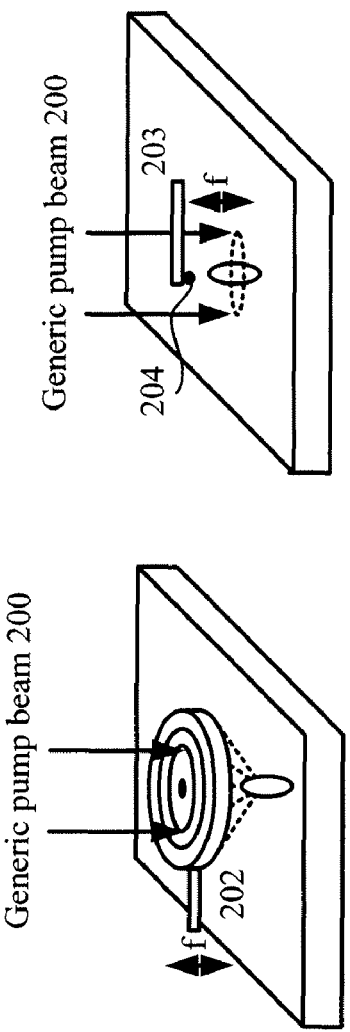
FIG. 2B illustrates an exemplary near-field generation device as implemented by a laser diode device.
Figure 2A:
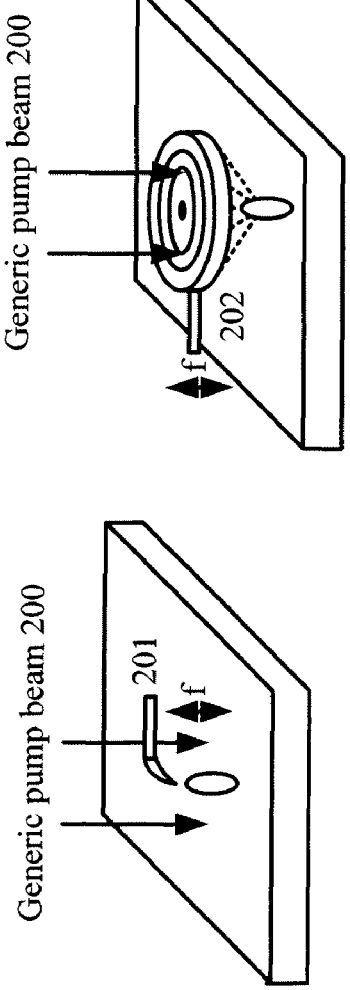
FIG. 2A illustrates an exemplary near-field generation device as implemented by a tip enhancement device.

In one embodiment, the near-field generation device can be implemented using a field enhancement tip device 201, which is shown in FIG. 2A in the context of a generic pump beam 200. For example, a laser-irradiated tip ending with a nanometer scale can provide a local enhancement of the electric field by several orders of magnitude. An exemplary laser-irradiated tip is described in "Near Field Raman spectroscopy using a sharp metal tip" A. Hartschuh, N. Anderson and L. Novotny, Journal of Microscopy, 210, 234 (2003). Notably, optical excitation in the tip-sample cavity at near-field configuration provides local field confinement near the tip apex. Field confinement can be defined by the sharpness of the tip. Field distribution can be approximated by the field of a dipole oriented in direction of tip axis and located in the center of the tip apex. Notably, the tip material is not limited to metal. For example, the tip material could comprise a dielectric or semiconductor material, as described in "Contrast and scattering efficiency of scattering-type near-field optical probes", by D. Haefliger, J. M. Plitzko and R. Hillenbrand, Appl. Phys. Lett. 85, 4466 (2004). The tip material could also be a semiconductor tip coated with various materials, as described in "Material Specific mapping of metal/semiconductor/dielectric nanosystems at 10 nm resolution by back-scattering near-field optical microscopy" by R. Hillenbrand and F. Keilmann, Appl. Phys. Lett. 80, 25 (2002), and in "Near-field probing of vibrational absorption for chemical microscopy", by B. Knoll and F. F. Keilmann, Nature 399, 134 (1999). The tip material could also be metal or dielectrics and semiconductors coated with thin metal films Advantageously, the confined light source generated by field enhancement tip device 201 can provide a very small spot, i.e. beyond spatial resolution limited by the electromagnetic wavelength. Additionally, field enhancement tip device 201 can provide significant flexibility in the probing depth of the sample surface by varying the tip-to-sample distance. Note that the wavelength of generic pump beam 204 can also be varied to provide yet further flexibility.

Note that in addition to field enhancement, the sharp tip of field enhancement tip device 201 can also advantageously serve as an atomic force microscopy (AFM) tip, which can provide nano-scale imaging means for locating the small features to be measured that are un-resolvable by conventional visible optical microscopy.

In another embodiment, the near-field generation device can be implemented using a laser diode device 202, as shown in FIG. 2B. Laser diode device 202 can include a small aperture surrounded by rings with specific geometry dimensions to resonantly excite surface plasmon polarions. This excitation can generate a highly condensed output light with sub-wavelength lateral width. An exemplary laser diode device is described "Plasmonic very-small-aperture lasers", by B. Guo, G. Song, and L. Chen, Appl. Phys. Lett. 91, 061124 (2007). In one embodiment, laser diode device 202 can be implemented as a vertical cavity surface emitting laser (VCSEL) at the end of an AFM tip to provide the modulation frequency f.

In yet another embodiment shown in FIG. 2C, the near-field generation device can include a cantilevered probe 203 with a pre-engineered nanostructure 204 on the tip as described in "Controlled fabrication of Silver or Gold nano-particle near-field optical atomic force probes: Enhancement of second-halmonic generation", by A. Barsegova, A. Lewis, A. Khatchatouriants, A. Manevitch, A. Ignatov, N. Axelrod and C. Sukenik, Appl. Phys. Lett. 81, 3461 (2002).

Another exemplary local electric field enhancement device may be created by mounting a solid immersion lens to an optical fiber. The assembly is the attached to AFM probe, as described, for example, in "Applying solid immersion near-field optics to Raman analysis of strained silicon thin films", by G. M. Lerman, A. Israel and A. Lewis, Appl. Phys. Lett. 89, 223122 (2006).

Figure 2F:
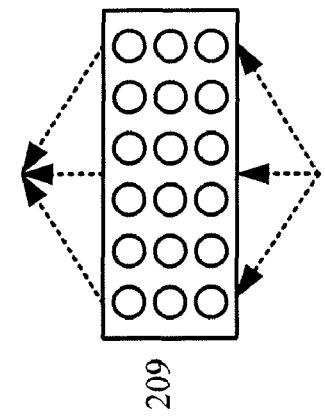
FIG. 2F illustrates an exemplary near-field generation device as implemented by a two-dimensional photonic-crystal-based superlens.
Figure 2E:
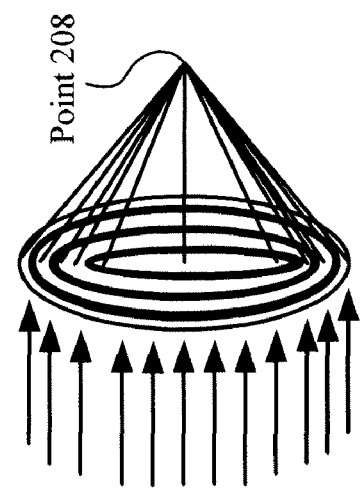
FIG. 2E illustrates an exemplary near-field generation device as implemented by a plasmonic micro zoneplate.
Figure 2D:
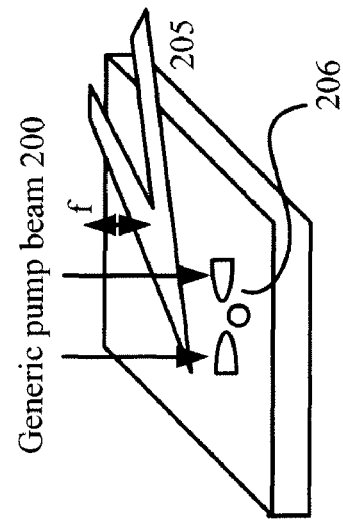
FIG. 2D illustrates an exemplary near-field generation device as implemented by a "bowtie" antenna.

In yet another embodiment shown in FIG. 2D, the near-field generation device can be implemented using a nano "bowtie" antenna 206. An exemplary "bowtie" antenna and some other exemplary local electric field enhancement antennas are described in "Optical antennas: Resonators for local field enhancement", by K. B. Crozier, A. Sundaramurthy, G.

S. Kino and C. F. Quate, J. Appl. Phys. 94, 4632 (2003). The nano "bowtie" antenna can be made of a single "bowtie" or arrays of "bowtie" supported on a substrate compatible to the wavelength used in the pump beam. The nano "bowtie" antenna can be then mounted on the cantilevered tip of an AFM probe 205.

In yet another embodiment shown in FIG. 2E, the near-field generation device can be implemented using a plasmonic micro zoneplate 207. Plasmonic micro zoneplate 207 is analogous to a Fresnel zoneplate in that it has alternating transparent and opaque zones with gradual decreasing outer zone width ΔR. However, plasmonic micro zoneplate 207 differs from a conventional zone plate in that the opaque zones are made of a noble metal film. An exemplary plasomonic micro zoneplate is described in "Plasmonic micro-zone plate: superfocusing at visible regime", by Y. Fu, W. Zhou, and L. Lim, Appl. Phys. Lett., 91, 061124 (2007). Notably, these noble metal zones can advantageously regenerate evanescent waves to achieve sub-wavelength focusing in the near-field (focus at point 208 in FIG. 2E). In one embodiment, plasmonic micro zoneplate 207 can be placed at the end of an AFM tip (not shown in FIG. 2E) to provide the modulation frequency f.

In yet another embodiment shown in FIG. 2F, the near-field generation device can be implemented using a two-dimensional photonic-crystal-based superlens 209. An exemplary superlens is described in "All-angle beam refocusing in uniform triangular photonic crystal slabs", by R. Zengerle and P. C. Hoang, JOSA B 24, 997 (2007). In one embodiment, photonic-crystal-based superlens 209 can be placed at the end of an AFM tip (not shown in FIG. 2F) to provide the modulation frequency f.

In yet another embodiment, the near-field generation device can be implemented using evanescent-field lenses (near-field plates). Exemplary evanescent-field lenses are described in "Radiation-less electromagnetic interference: evanescent-field lenses and perfect focusing", by R. Merlin, Science 317, 927 (2007). Near-field focusing plates are planar (grating-like) structures that can focus electromagnetic radiation to spots or lines of arbitrarily small sub-wavelength dimension. Furthermore, those lenses can be tailored to give sub-wavelength focal patterns of various types.

Figure 3:
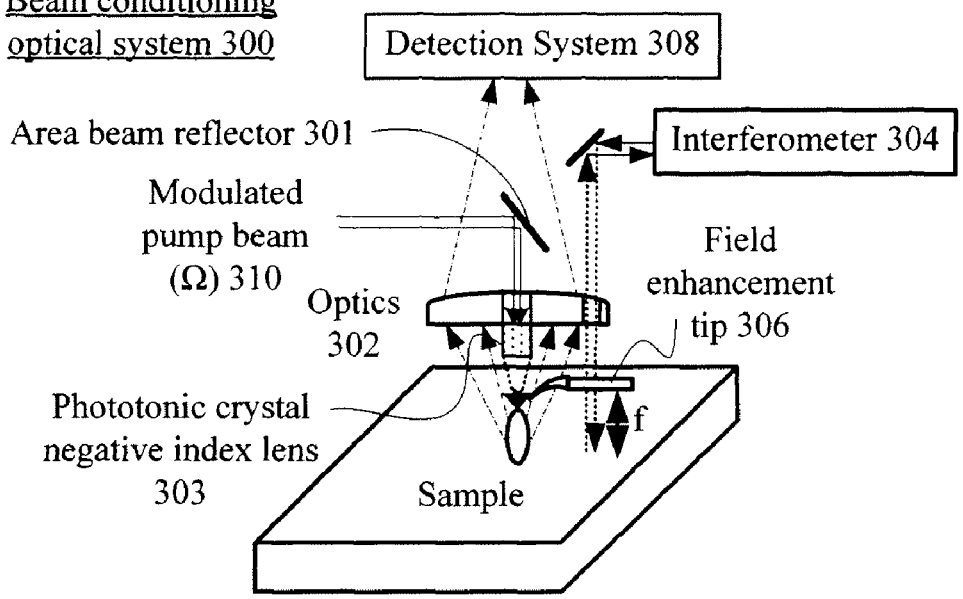
FIG. 3 illustrates an exemplary beam conditioning optical system including a photonic crystal negative refractive index lens.

Advantageously, the nano-scale navigation and control features provided by the above-described implementations of the near-field generation device can achieve optimized measurement capability. To provide yet further optimization, a beam conditioning optical system can be included in the pump beam path. In one embodiment shown in FIG. 3, an exemplary beam conditioning optical system 300 can include an area beam reflector 301, optics 302, a photonic crystal negative refractive index lens 303, and an interferometer 304. Area beam reflector 301 reflects modulated pump beam 102 onto photonic crystal negative refractive index lens 303, which in turn focuses modulated pump beam 102 onto the sample. As shown in FIG. 3 for context, the near-field generation device (for illustration purposes, a field enhancement tip 306 is shown) can be located in the optical path of photonic crystal negative refractive index lens 303 to further condition a modulated pump beam 310. The dark-field scattered signals (which contains components modulated at Ω+f and Ω−f) are collected by detection system 308 to generate a dark field image. Advantageously, lens 303 can provide optimized focusing without diffraction. Interferometer 304 (and its associated mirror, which is shown, but not labeled) can be included to ensure that beam conditioning optical system 300 maintains a safe distance from sample 110 using an optical feedback (e.g. through optics 302, as shown). Beam conditioning optical system 300 can advantageously provide excellent sub-wavelength resolution image of the measurement area as well as provide fine focusing adjustment.

Note that beam conditioning optical system 300 can have applications in addition to near-field spectroscopy. For example, when mounted on a microscope, beam conditioning optical system 300 can be used to locate nanometer-scale structures (e.g. test structures) on an integrated chip and then provide dark field images with high resolution of such structures.

Figure 4:
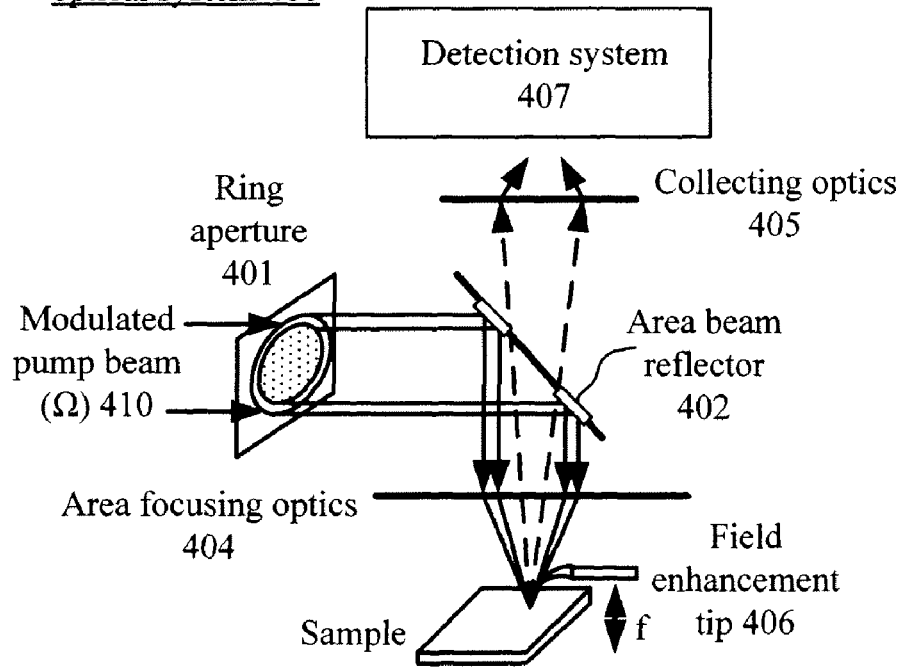
FIG. 4 illustrates an exemplary beam conditioning optical system including a ring aperture and area reflectors.

FIG. 4 illustrates another beam conditioning optical system 400 that can be used with a modulated pump beam 410. In this embodiment, beam conditioning optical system 400 can include a ring aperture 401, an area beam reflector 402 (e.g. a ring mirror), area focusing optics 404, and collecting optics 405. In the configuration shown in FIG. 4, area beam reflector 402 receives a modulated pump beam 410 as output by ring aperture 401 and directs modulated pump beam 410 to area focusing optics 404. Area focusing optics 404 can then focus modulated pump beam 410 onto the sample and near the tip of the near-field generation device (for illustration purposes, a field enhancement tip 306 is shown field enhancement tip device 406). In the context of field enhancement tip 406, the enhanced electromagnetic wave interacts with the sample. The resulting, scattered light from the sample is collected by collecting optics 405 and then directed to a detection system 407 (shown for context). Note that in this non-limiting embodiment, beam conditioning optical system 400 is working in a dark-field mode.

As described above, a near-field, heterodyne spectroscopy system can advantageously provide very small spot measurement, i.e. smaller than the dimension imposed by the diffraction limit from wavelength used spanning from DUV to THz in electromagnetic spectrum. Notably, the excitation to the modulated probe beam is near-field by nature. Therefore, the electric field in the material of the sample is evanescent, i.e. experiences exponential decay with distance. As a result, the probing depth is shallower than that of far-field excitation. With luminous material or high-scatter material, the near-field excitation approach also advantageously eliminates the background signal getting into the detector.

Note that a near-field technique can have lower throughput than a far-field technique (because the near-field technique includes scanning). However, the above-described near-field generation device configurations can provide navigation and imaging capability with accuracy far exceeding conventional far-field systems and therefore have significant advantages over far-field systems even in light of the throughput.

Any of the embodiments described herein may be used for measuring films and structures on substrates. The measurements may include, but are not limited to, measuring properties such as thickness, film composition, strain, carrier mobility, carrier density, critical dimensions and overlay. Specifically, the disclosed embodiments could be used to measure local stress in shallow-trench-isolation (STI) and Silicon-On-Insulator (SOI) structures. Near-field Raman spectroscopy as disclosed herein may also be used for measuring strain, stress, material composition and local order in advanced nano-structured materials, such as carbon nanotubes and graphene sheets, group III-V compounds like gallium arsenide, group II-VI compounds, organic materials or mixtures of such materials.

The above-described near-field, heterodyne spectroscopy systems advantageously provide excitation that is near-field by nature, which results in an electric field in the sample that is evanescent. Therefore, the probing depth is shallower than that of far-field excitation. With luminous material or high-scatter material, the near-field excitation techniques can also advantageously eliminate background signals getting into the detector.

Although illustrative embodiments of the invention have been described in detail herein with reference to the accompanying figures, it is to be understood that the invention is not limited to those precise embodiments. They are not intended to be exhaustive or to limit the invention to the precise forms disclosed. As such, many modifications and variations will be apparent.

For example, in one embodiment, the near-field generation device could be implemented using a nano-particle of gold or any one of known small-spot-generating apertures (e.g. a C aperture) mounted on the end of an AFM tip. Note that the near-field generation device could be combined with monochromatic light (e.g. the implementation of FIG. 2A), a heterodyne laser (e.g. the implementation of FIG. 2A), or a broadband source (e.g. the implementation of FIG. 2B). In any of these light sources, the near-field generation device can provide an electromagnetic wave spanning over a broad spectral range, e.g. from DUV to millimeter wave (THz).

In one embodiment, the photonic crystal negative index lens shown in FIG. 3 could be replaced by plasmatic micro zoneplates (see, e.g. FIG. 2B), a plasmonic very-small-aperture laser assembly (see, e.g. FIG. 2C), or an evanescent field lens.

In another embodiment, the pump beam source and the probe beam source each receive modulation frequencies (e.g. $\Omega_1$ and $\Omega_2$). In this embodiment, the reflected probe beam has components at one or more frequencies involving sums and differences of $\Omega_1$, $\Omega_2$ and f (i.e. $\pm\Omega_1\pm\Omega_2\pm f$).

Accordingly, it is intended that the scope of the invention be defined by the following Claims and their equivalents.

The invention claimed is:

1. A near-field, heterodyne spectroscopy system comprising:
    a probe beam source for generating a probe beam and directing the probe beam to a point on a sample;
    a pump beam source for generating a modulated pump beam and directing the modulated pump beam to the point on the sample;
    a near-field generation device for receiving the modulated pump beam, generating a modulated near-field beam having a near-field component, and directing the modulated near-field beam to the point on the sample;
    a detection system for detecting a reflected probe beam from the point on the sample, the reflected probe beam resulting from the probe beam, the modulated pump beam, and the near-field generation beam; and
    a processor for performing demodulation of the detected reflected probe beam and analyzing the sample based on the demodulation.

2. The near-field, heterodyne spectroscopy system of claim 1, wherein the near-field generation device is modulated at a frequency f which is different from the modulation frequency of the pump beam source.

3. The near-field, heterodyne spectroscopy system of claim 1, wherein the near-field generation device includes a field enhancement tip device.

4. The near-field, heterodyne spectroscopy system of claim 1, wherein the near-field generation device includes a laser-irradiated tip ending with a nanometer scale.

5. The near-field, heterodyne spectroscopy system of claim 1, wherein the near-field generation device includes a laser diode device.

6. The near-field, heterodyne spectroscopy system of claim 1, wherein the near-field generation device includes an aperture surrounded by rings that resonantly excite surface plasmon polarions.

7. The near-field, heterodyne spectroscopy system of claim 1, wherein the near-field generation device includes a plasmonic micro zoneplate.

8. The near-field, heterodyne spectroscopy system of claim 1, wherein the near-field generation device includes a two-dimensional photonic-crystal-based superlens.

9. The near-field, heterodyne spectroscopy system of claim 1, further including a beam conditioning optical system that conditions the pump beam for the near-field generation device.

10. The near-field, heterodyne spectroscopy system of claim 9, wherein the beam conditioning optical system includes a photonic crystal negative refractive index lens that generates a dark-field image.

11. The near-field, heterodyne spectroscopy system of claim 9, wherein the beam conditioning optical system includes a ring aperture.

12. A method of performing spectroscopy on a sample, the method comprising:
    generating a probe beam and directing the probe beam to a point on the sample;
    generating a modulated pump beam having a modulation frequency $\Omega$ and directing the modulated pump beam to the point on the sample;
    generating a modulated near-field beam using the modulated pump beam and an additional modulation frequency f, wherein the modulated near-field beam has near-field components (f+$\Omega$) and ($\Omega$−f), and directing the modulated near-field beam to the point on the sample;
    detecting a reflected probe beam from the point on the sample, the reflected probe beam resulting from the probe beam, the modulated pump beam, and the near-field generation beam;
    demodulating the reflected probe beam; and
    analyzing the sample based on the demodulating.

13. A near-field, heterodyne spectroscopy system comprising:
    a pump beam source for generating a modulated pump beam and directing the modulated pump beam to a point on a sample;
    a near-field generation device for receiving the modulated pump beam, generating a modulated near-field beam having a near-field component, and directing the modulated near-field beam to the point on the sample;
    a detection system for detecting a reflected pump beam from the point on the sample, the reflected pump beam resulting from the modulated pump beam and the modulated near-field beam; and
    a processor for performing demodulation of the detected reflected pump beam and analyzing the sample based on the demodulation.

14. The near-field, heterodyne spectroscopy system of claim 13, wherein the near-field generation device is modulated at a frequency f which is different from the modulation frequency of the pump beam source.

15. The near-field, heterodyne spectroscopy system of claim 13, wherein the near-field generation device includes a field enhancement tip device.

16. The near-field, heterodyne spectroscopy system of claim 13, wherein the near-field generation device includes a laser-irradiated tip ending with a nanometer scale.

17. The near-field, heterodyne spectroscopy system of claim 13, wherein the near-field generation device includes a laser diode device.

18. The near-field, heterodyne spectroscopy system of claim 13, wherein the near-field generation device includes an aperture surrounded by rings that resonantly excite surface plasmon polarions.

19. The near-field, heterodyne spectroscopy system of claim 13, wherein the near-field generation device includes a plasmonic micro zoneplate.

20. The near-field, heterodyne spectroscopy system of claim 13, wherein the near-field generation device includes a two-dimensional photonic-crystal-based superlens.

21. The near-field, heterodyne spectroscopy system of claim 13, further including a beam conditioning optical system that conditions the pump beam for the near-field generation device.

22. The near-field, heterodyne spectroscopy system of claim 21, wherein the beam conditioning optical system includes a photonic crystal negative refractive index lens that generates a dark-field image.

23. The near-field, heterodyne spectroscopy system of claim 21, wherein the beam conditioning optical system includes a ring aperture.

24. A method of performing spectroscopy on a sample, the method comprising:
generating a modulated pump beam having a modulation frequency $\Omega$ and directing the modulated pump beam to a point on a sample;
generating a modulated near-field beam using the modulated pump beam and an additional modulation frequency f, wherein the near-field beam has near-field components (f+$\Omega$) and ($\Omega$−f), and directing the modulated near-field beam to the point on the sample;
detecting a reflected pump beam from the point on the sample, the reflected pump beam resulting from the modulated pump beam and the modulated near-field beam;
demodulating the reflected pump beam; and
analyzing the sample based on the demodulating.

25. A near-field, heterodyne spectroscopy system comprising:
a probe beam source for generating a modulated probe beam and directing the modulated probe beam to a point on a sample;
a pump beam source for generating a pump beam and directing the modulated probe beam to the point on the sample;
a near-field generation device for receiving the pump beam, generating a modulated near-field beam having a near-field component based on the pump beam and an additional modulation frequency, and directing the modulated near-field beam to the point on the sample;
a detection system for detecting a reflected probe beam from the point on the sample, the reflected probe beam resulting from the modulated probe beam, the pump beam, and the near-field modulation beam; and
a processor for performing demodulation of the detected reflected probe beam and analyzing the sample based on the demodulation.

26. The near-field, heterodyne spectroscopy system of claim 25, wherein the near-field generation device is modulated at a frequency f which is different from the modulation frequency of the probe beam source.

27. The near-field, heterodyne spectroscopy system of claim 25, wherein the near-field generation device includes a field enhancement tip device.

28. The near-field, heterodyne spectroscopy system of claim 25, wherein the near-field generation device includes a laser-irradiated tip ending with a nanometer scale.

29. The near-field, heterodyne spectroscopy system of claim 25, wherein the near-field generation device includes a laser diode device.

30. The near-field, heterodyne spectroscopy system of claim 25, wherein the near-field generation device includes an aperture surrounded by rings that resonantly excite surface plasmon polarions.

31. The near-field, heterodyne spectroscopy system of claim 25, wherein the near-field generation device includes a plasmonic micro zoneplate.

32. The near-field, heterodyne spectroscopy system of claim 25, wherein the near-field generation device includes a two-dimensional photonic-crystal-based superlens.

33. The near-field, heterodyne spectroscopy system of claim 25, further including a beam conditioning optical system that conditions the pump beam for the near-field generation device.

34. The near-field, heterodyne spectroscopy system of claim 33, wherein the beam conditioning optical system includes a photonic crystal negative refractive index lens that generates a dark-field image.

35. The near-field, heterodyne spectroscopy system of claim 33, wherein the beam conditioning optical system includes a ring aperture.

36. A method of performing spectroscopy on a sample, the method comprising:
generating a modulated probe beam having a modulation frequency $\Omega$ and directing the modulated probe beam to a point on the sample;
generating a pump beam;
generating a modulated near-field beam using the pump beam and a modulation frequency f, and directing the modulated near-field generation beam to the point on the sample;
detecting a reflected probe beam from the point on the sample, the reflected probe beam resulting from the modulated probe beam, the pump beam, and the modulated near-field beam;
demodulating the reflected probe beam; and
analyzing the sample based on the demodulating.

* * * * *